US 6,898,271 B2

(12) United States Patent
Akutsu et al.

(10) Patent No.: US 6,898,271 B2
(45) Date of Patent: May 24, 2005

(54) X-RAY RADIOGRAPHIC APPARATUS, X-RAY RESTRICTOR, AND X-RAY RADIOGRAPHIC METHOD

(75) Inventors: Kouji Akutsu, Nara (JP); Wataru Miyamoto, Kusatsu (JP); Masayuki Yasumi, Kyoto (JP); Tetsu Nakayama, Kyoto (JP); Isao Nakata, Kyoto (JP); Mitsuru Umeda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/404,475

(22) Filed: Apr. 1, 2003

(65) Prior Publication Data

US 2004/0005031 A1 Jan. 8, 2004

(30) Foreign Application Priority Data

May 29, 2002 (JP) ........................................ 2002-155635

(51) Int. Cl.[7] .................................................. G21K 3/00
(52) U.S. Cl. ........................................ 378/157; 378/159
(58) Field of Search .................................. 378/156–159

(56) References Cited

U.S. PATENT DOCUMENTS

| | | | | | |
|---|---|---|---|---|---|
| 4,329,590 | A | * | 5/1982 | Adelmeyer | .................. 378/91 |
| 5,185,775 | A | * | 2/1993 | Sirvin | ......................... 378/156 |
| 5,195,121 | A | * | 3/1993 | Charrier | ..................... 378/160 |
| 6,633,627 | B2 | * | 10/2003 | Horiuchi | ..................... 378/156 |

* cited by examiner

Primary Examiner—Craig E. Church
Assistant Examiner—Jurie Yun
(74) Attorney, Agent, or Firm—Rankin, Hill, Porter & Clark LLP

(57) ABSTRACT

A switching mechanism is configured such that a lower limb radiographic filter 11a is moved inside a radiation field of the X-rays that is an opening portion of an X-ray movable restriction only when radiographing a region of a subject from the groin to the toe, or the filter is moved outside the radiation field when radiographing the lumber region of the subject. With this switching mechanism thus constituted, it is possible to lighten a burden of the operator, and realize the X-ray radiographic apparatus having high universality.

4 Claims, 5 Drawing Sheets

X-RAY RADIOGRAPHIC APPARATUS, X-RAY RESTRICTOR, AND X-RAY RADIOGRAPHIC METHOD

BACKGROUND OF THE INVENTION

1. Field of the Invention

The present invention relates to an X-ray radiographic apparatus and an X-ray radiographic method for radiographing a subject by detecting an X-ray applied from an X-ray tube to the subject, and more particularly to a technique for performing an X-ray radiography of the subject, employing a filter for extracting the X-ray components, and also relates to an X-ray restrictor used in the X-ray radiographic apparatus.

2. Description of the Related Art

In related art, when the X-ray radiographic apparatus is employed to make the angiography for the lower limb, simultaneously for both legs, a contrast medium is injected into the blood vessel of the subject, and the contrast medium flowing within the blood vessel from the lumber region to the toe is radiographed with the X-ray radiographic apparatus. During this radiography, a holding member (e.g., C-type arm) for holding an X-ray tube and an X-ray detector (image intensifier) for the X-ray radiographic apparatus, or a table top board for laying the subject thereon is being moved continuously or stepwise from the lumber region to the toe.

However, the related-art X-ray radiographic apparatus had a problem that when the radiography is performed using a filter for extracting the X-ray components, the operator had a burden with the operation of the filter and the radiography becomes difficult. For example, when the angiography for the lower limb is made simultaneously for both legs, some halation occurs in the radiographed image because the transmission factor of X-rays is different between a leg portion and a portion between both legs. To prevent the halation, if a specific mat is placed between both legs of the subject, the operator has more burden with the mat. Also, the halation may be prevented by placing the filter near a bulb of the X-ray tube, in which the center of the radiographed image of the lumber region is hidden by the filter, making the radiography difficult.

SUMMARY OF THE INVENTION

This invention has been achieved in the light of these affairs, and it is an object of the invention to provide an X-ray radiographic apparatus and X-ray radiographic method with high universality in which a burden of the operator is lightened, and also provide an X-ray restrictor used in the X-ray radiographic apparatus.

In order to achieve the above object, this invention has the following constitution.

An X-ray radiographic apparatus, according to a first aspect of the invention, comprising:

an X-ray tube for radiating X-rays to a subject;

an X-ray detector for detecting an X-ray applied to the subject;

a holding member for holding the X-ray tube and the X-ray detector;

a table top board for laying the subject thereon;

a filter for extracting X-ray components radiated from the X-ray tube; and a movement mechanism for moving the filter outside or inside a radiation field of the X-rays radiated from the X-ray tube so that the filter is moved inside the radiation field, only when the relative position between the holding member and the table top board is at a predetermined position, and the filter is moved outside the radiation field, when the relative position is other than the predetermined position.

With the invention of the first aspect, the movement mechanism moves the filter outside or inside the radiation field of the X-rays radiated from the X-ray tube, wherein the movement mechanism is configured such that the filter is moved inside the radiation field, only when the relative position between the holding member and the table top board is at a predetermined position, or the filter is moved outside the radiation field, when the relative position is other than the predetermined position. Accordingly, to acquire the radiographed image at the predetermined position employing the filter, the movement mechanism moves the filter inside the radiation field only at the predetermined position, thereby performing an X-ray radiography of the subject at the predetermined position through the filter. Further, to acquire the radiographed image other than at the predetermined position without employing the filter, the movement mechanism moves the filter outside the radiation field other than at the predetermined position, thereby performing an X-ray radiography of the subject other than at the predetermined position without the filter. Consequently, it is possible to lighten a burden of the operator who places a mat on the subject as performed in the related art, and further to select whether or not to use the filter depending on the radiographing position, thereby facilitating the radiography, whereby the X-ray radiographic apparatus has a higher universality.

The filter is not specifically limited, as long as the X-rays having a specific energy, or the X-ray components, can be extracted from the X-ray flux that is different for each wavelength of the X-rays. For example, the filter may restrict the X-ray flux radiated from the X-ray tube in a predetermined shape. The "restrict in a predetermined shape" may involve setting a higher transmission factor of the X-rays within the predetermined shape and a lower or null transmission factor of the X-ray outside the predetermined shape, or setting a higher transmission factor of the X-rays outside the predetermined shape and a lower or null transmission factor of the X-ray within the predetermined shape.

Further, the movement mechanism may include a switching member for selectively switching a plurality of filters into a certain filter to move the filter inside or outside the radiation field of the X-rays. In this manner, various filters may be employed to perform the X-ray radiography.

In this specification, the inventions regarding an X-ray radiographic method, the X-ray tube for use in the X-ray radiographic apparatus, and the X-ray restrictor are also disclosed.

(1) An X-ray radiographic method for performing an X-ray radiography of a subject, comprising:

radiating X-rays from an X-ray tube to the subject;

detecting an X-ray applied to the subject with an X-ray detector;

moving at least one of a holding member for holding the X-ray tube and the X-ray detector and a table top board for laying the subject thereon;

moving a filter, which extracts X-ray components radiated from the X-ray tube, outside or inside a radiation field of the X-rays radiated from the X-ray tube so that the filter is moved inside the radiation field, only when the relative position between the holding member and the table top board is at a predetermined position, or the filter is moved outside the radiation field, when the relative position is other than the predetermined position.

With the invention (1), to acquire the radiographed image at the predetermined position employing the filter, the filter is moved inside the radiation field only at the predetermined position, thereby performing an X-ray radiography of the subject at the predetermined position through the filter, or to acquire the radiographed image other than at the predetermined position without employing the filter, the filter is moved outside the radiation field other than at the predetermined position, thereby performing an X-ray radiography of the subject other than at the predetermined position without the filter. Consequently, it is possible to lighten a burden of the operator who places a mat on the subject as performed in the related art, and further to select whether or not to use the filter depending on the radiographing position, thereby facilitating the radiography.

(2) The X-ray radiographic method as defined in (1), may comprise selectively switching a plurality of filters into a certain filter to move the filter inside or outside the radiation field of the X-rays.

With the invention (2), since the method includes selectively switching a plurality of filters into a certain filter to move the filter inside or outside the radiation field of the X-rays, various filters may be employed to perform the X-ray radiography.

(3) An X-ray tube for use in an X-ray radiographic apparatus comprising an X-ray detector, a holding member for holding the X-ray tube and the X-ray detector and a table top board for laying a subject thereon, the X-ray tube comprising:

an X-ray source for radiating X-rays to the subject;

a filter for extracting X-ray components radiated from an X-ray source; and a movement mechanism for moving the filter outside or inside a radiation field of the X-rays radiated from the X-ray source so that the filter is moved inside the radiation field, only when the relative position between the holding member and the table top board is at a predetermined position, and the filter is moved outside the radiation field, when the relative position is other than the predetermined position.

(4) An X-ray restrictor for controlling a radiation field of X-rays radiated from an X-ray tube of an X-ray radiographic apparatus, the X-ray radiographic apparatus comprising the X-ray tube, an X-ray detector, a holding member for holding the X-ray tube and the X-ray detector and a table top board for laying a subject thereon, the X-ray restrictor comprising:

a filter for extracting X-ray components radiated from the X-ray tube; and a movement mechanism for moving the filter outside or inside the radiation field of the X-rays radiated from the X-ray tube so that the filter is moved inside the radiation field, only when the relative position between the holding member and the table top board is at a predetermined position, and the filter is moved outside the radiation field, when the relative position is other than the predetermined position.

With the inventions (3) and (4), the movement mechanism is configured such that the filter is moved inside the radiation field, only when the relative position between the holding member and the table top board is at a predetermined position, or the filter is moved outside the radiation field, when the relative position is other than the predetermined position. Consequently, it is possible to lighten a burden of the operator, and realize the X-ray tube and the X-ray restrictor having a higher universality.

(5) The X-ray tube as defined in (3), wherein the filter may restrict an X-ray flux radiated from the X-ray tube in a predetermined shape.

(6) The X-ray restrictor as defined in (4), wherein the filter may restrict an X-ray flux radiated from the X-ray tube in a predetermined shape.

The filter as defined in (3) and (4) is not specifically limited, like the filter of the first aspect of the invention, but may restrict the X-ray flux radiated from the X-ray tube in a predetermined shape, like the inventions (5) and (6).

(7) The X-ray tube as defined in (3) or (5), wherein the movement mechanism may include a switching member for selectively switching a plurality of filters into a certain filter.

(8) The X-ray restrictor as defined in (4) or (6), wherein the movement mechanism may include a switching member for selectively switching a plurality of filters into a certain filter.

With the inventions (7) and (8), the movement mechanism is constituted of a switching member for selectively switching a plurality of filters into a certain filter to move the filter inside or outside the radiation field of the X-rays. In this manner, various filters may be employed to perform the X-ray radiography.

DETAILED DESCRIPTION OF THE INVENTION

One embodiment of the present invention will be described below with reference to the accompanying drawings.

Figure 1:
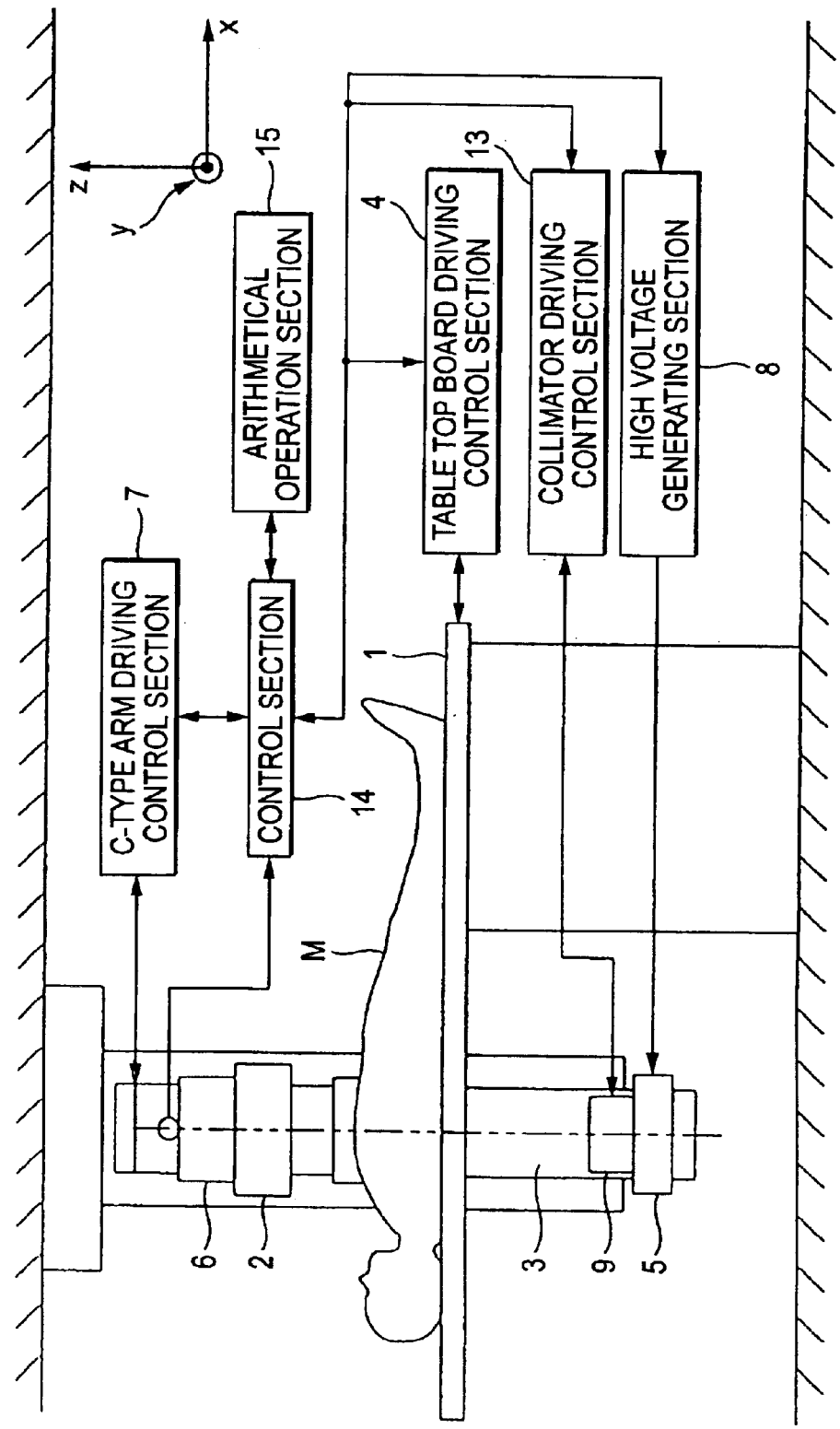
FIG. 1 is a side view showing the schematic constitution of an X-ray radiographic apparatus according to an embodiment of the invention.
Figure 2:
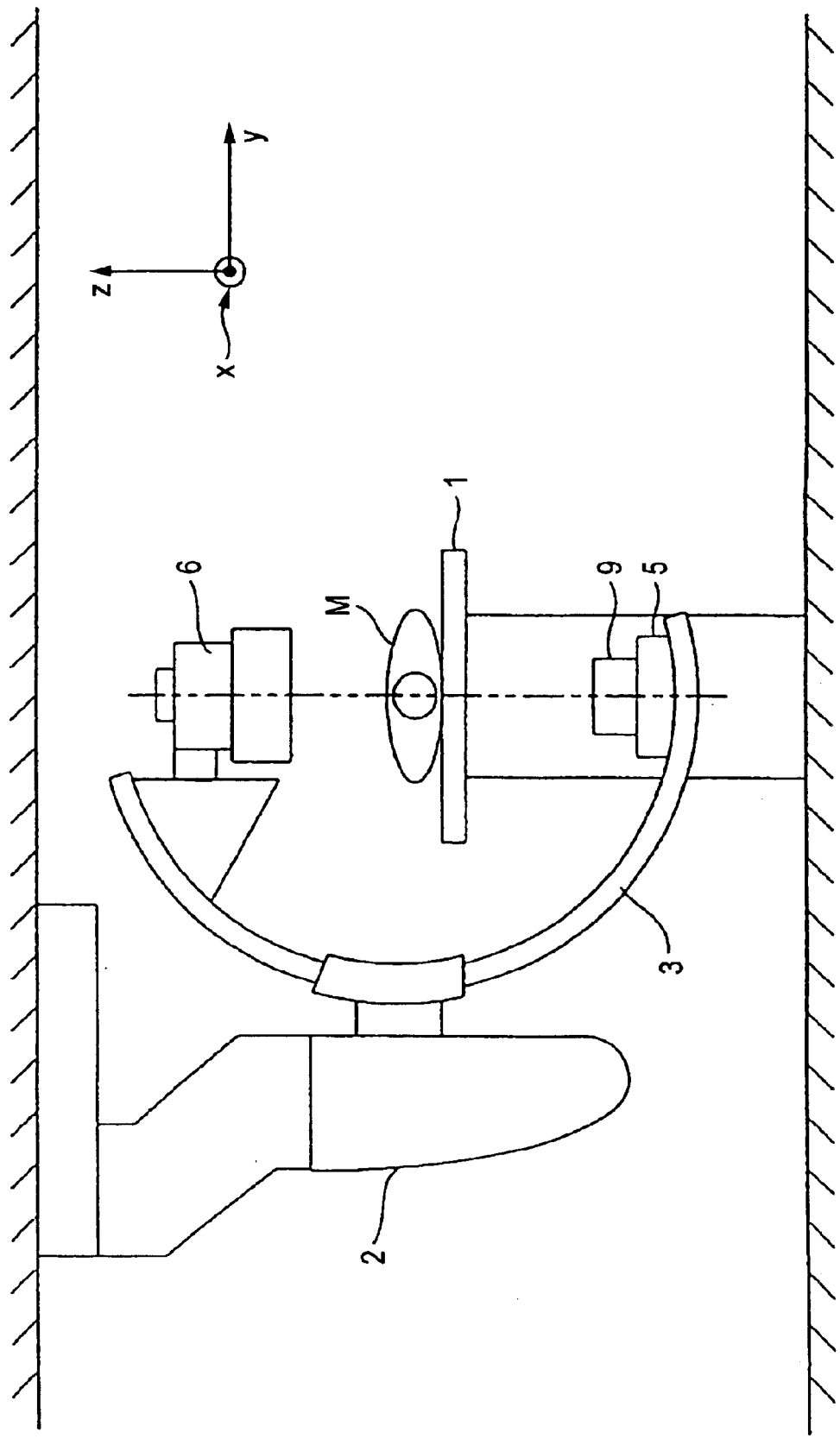
FIG. 2 is a front view showing the schematic constitution of the X-ray radiographic apparatus according to the embodiment of the invention.
Figure 3:
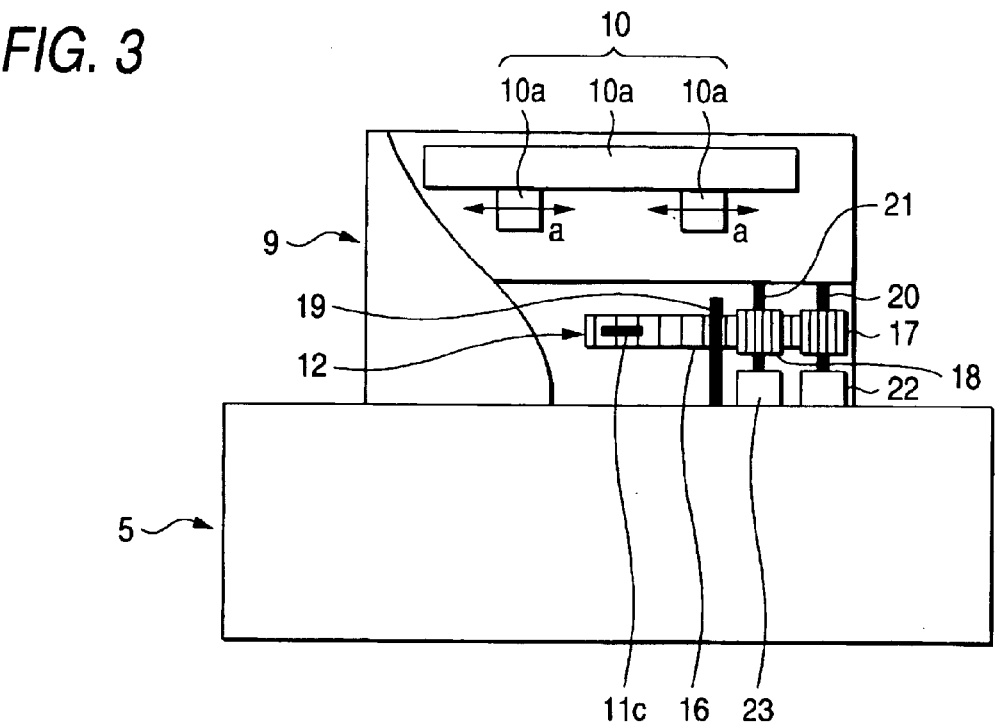
FIG. 3 is a view, partially broken away, of an X-ray tube and a collimator for use in the X-ray radiographic apparatus according to the embodiment of the invention.
Figure 4:
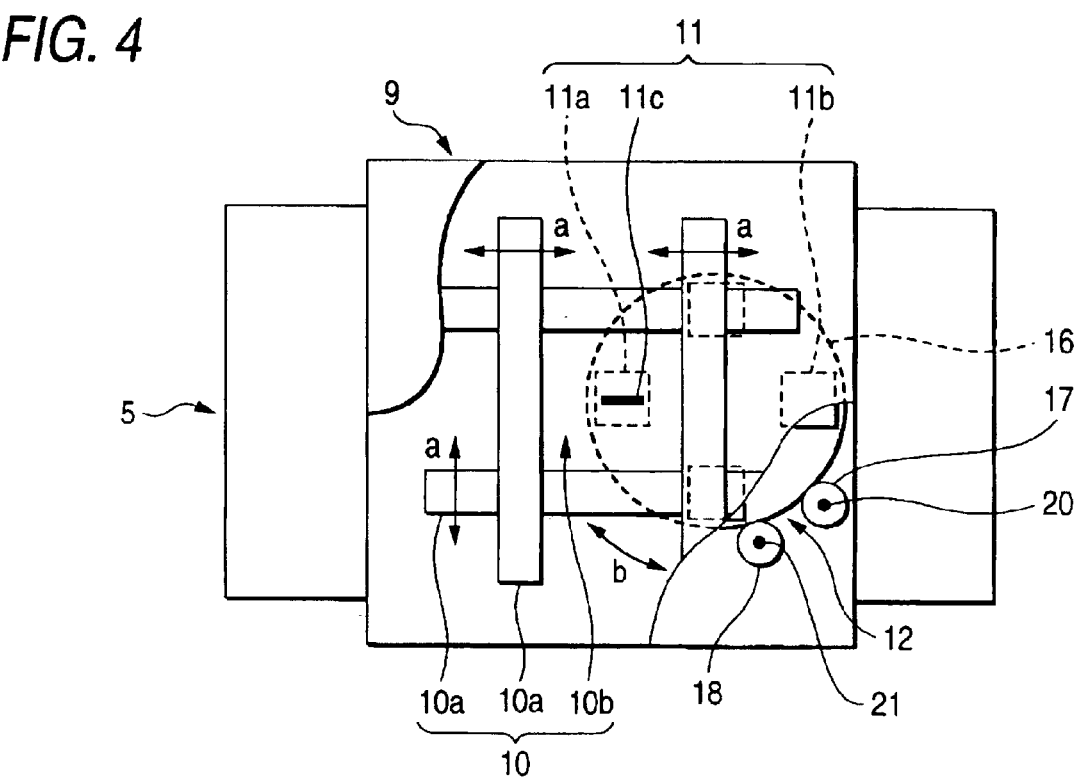
FIG. 4 is a plan view of the X-ray tube and the collimator according to the embodiment.
Figure 5A:
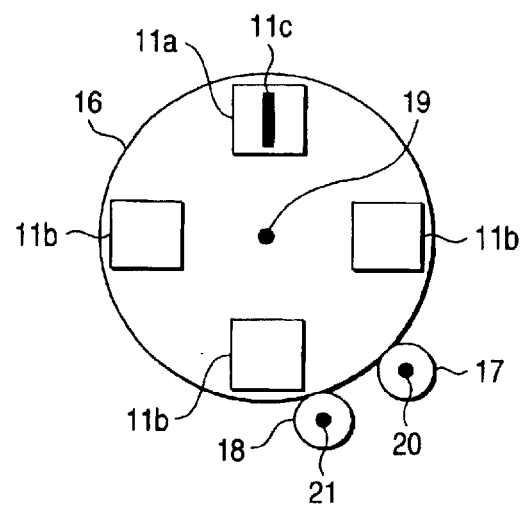
FIG. 5A is a plan view of a switching mechanism equipped within the collimator according to the embodiment in a state before the filter is switched.
Figure 5B:
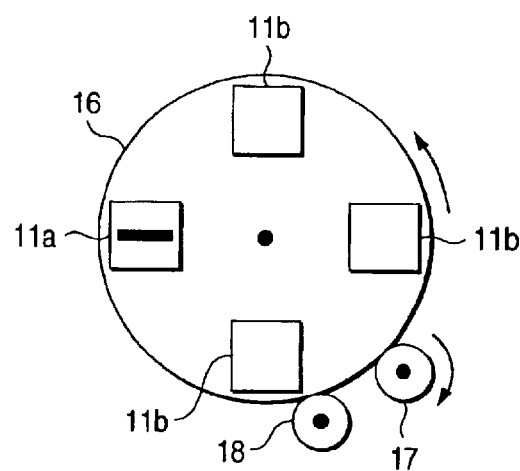
FIG. 5B is a plan view of a switching mechanism equipped within the collimator according to the embodiment in a state when the filter is switched.

FIG. 1 is a side view showing the schematic constitution of an X-ray radiographic apparatus according to an embodiment of the invention, and FIG. 2 is a front view thereof. FIG. 3 is a view, partially broken away, of an x-ray tube and a collimator for use in the X-ray radiographic apparatus according to the embodiment of the invention, and FIG. 4 is a plan view thereof. FIGS. 5A and 5B are plan views of a switching mechanism equipped within the collimator. In this embodiment, an X-ray radiographic apparatus will be exemplified in which a blood vessel image is radiographed by injecting a contrast medium into the subject via a catheter for injecting the contrast medium. This X-ray radiographic apparatus comprises a table top board 1 for laying the subject thereon for medical examination, a strut portion 2, and a C-type arm 3, as shown in FIGS. 1 and 2. This strut portion 2 is attached to a ceiling plane and fixed except for rotation around the axial center of a vertical axis (z-axis in FIGS. 1 and 2). The C-type arm 3 corresponds to a holding member of the invention.

The table top board 1 can be moved up and down and also moved along the body axis of the subject M. A table top board driving control section 4 is connected to the table top board 1 to control the driving of the table top board 1. The table top board driving control section 4 controls a driving mechanism for driving the table top board 1, a brake mechanism for stopping the movement of the table top board 1 in the body axis direction, a brake releasing mechanism for releasing the movement of the table top board 1 in the body axis direction, and a detection mechanism for detecting the position of the table top board 1 (not shown).

The X-ray tube 5 is supported at one end of the C-type arm 3 to radiate the X-rays to the subject M. An image intensifier 6 (hereinafter appropriately abbreviated as "I.I") is supported at the other end of the C-type arm 3 to detect the X-rays radiated on the subject M and convert them into an optical image. The C-type arm 3 can be rotated around the axial center of the body axis (x-axis in the FIGS. 1 and 2) of the subject M and also around the axial center of an axis (y-axis in FIGS. 1 and 2) in a perpendicular direction to the body axis of the subject M on the horizontal plane. The strut portion 2 can be rotated around the axial center of the vertical axis (z-axis in FIGS. 1 and 2). I.I 6 corresponds to an X-ray detector in this invention.

A C-type arm driving control section 7 is connected to the strut portion 2 and the C-type arm 3, respectively to control the driving of the strut portion 2 and the C-type arm 3. The C-type arm driving control section 7 controls a drive mechanism for driving the strut portion 2 and the C-type arm 3 and a detection mechanism for detecting the position of the strut portion 2 and the C-type arm 3 (not shown).

A high voltage generating section 8 is connected to the X-ray tube 5 to apply a bulb voltage and a bulb current to the X-ray tube 5. As shown in FIGS. 3 and 4, the X-ray tube 5 has a collimator 9 mounted on a plane in a direction for radiating the X-rays, in which this collimator 9 controls a radiation field of the X-rays. The collimator 9 comprises an X-ray movable restriction 10 having four plate-like members 10a and a switching mechanism 12 having a plurality of filters 11. The collimator 9 corresponds to an X-ray restrictor in this invention.

Four plate-like members 10a constituting the X-ray movable restriction 10 are disposed orthogonal to each other to have an opening portion 10b, each plate-like member 10a being movable in the direction of the arrow a in FIGS. 3 and 4. The X-rays passing through the opening portion 10b become the radiation field of the X-rays, each plate-like member 10a being movable to adjust the size of the opening portion 10b and thereby the radiation field of the X-rays.

As shown in FIGS. 1 and 2, a collimator drive control section 13 are connected to the plate-like members 10a and the switching mechanism 12, respectively to control the driving of the plate-like members 10a for the collimator 9 and the switching mechanism 12 (see FIGS. 3 and 4). The collimator drive control section 13 controls a drive mechanism (not shown) for driving the plate-like members 10a, a motor 22 for driving a base gear 16 of the switching mechanism 12, and a revolution counter 23 for detecting the position of the filter 11. A specific constitution of the switching mechanism 12 will be described later.

The data converted into an optical image by I.I 6 is passed via a control section 14 to an arithmetical operation section 15 for performing various arithmetical operations, and outputting as a radiographed image. The control section 14 totally controls the table top board driving control section 4, the C-type arm driving control section 7, the high voltage generating section 8, and the collimator driving control section 13. The arithmetical operation section 15 has a function of calculating the relative position between the C-type arm 3 and the table top board 1, on the basis of the positions of the C-type arm 3 and the table top board 1, besides the arithmetical operations.

Referring to FIGS. 3 to 5B, a specific constitution of the switching mechanism 12 will be described below. The switching mechanism 12 comprises the base gear 16 with a plurality of filters 11 disposed, a drive gear 17 and a position detecting gear 18 which are fitted with the base gear 16, a base shaft 19 passing through a central part of the base gear 16, a drive shaft 20 passing through a central part of the drive gear 17, a detection shaft 21 passing through a central part of the position detecting gear 18, a motor 22 for revolving the drive shaft 20 around the axial center, and the revolution counter 23 linked to the bottom of the detection shaft 21.

In this embodiment, the filter 11 disposed in the base gear 16 has a lower limb radiographic filter 11a and three additional filters 11b, as shown in FIG. 4. The lower limb radiographic filter 11a restrict an X-ray flux radiated from the X-ray tube 5 to the quadrilateral shape with a quadrilaterally-shaped hole near the center thereof. The three additional filters 11b regulate the degree of transmission of X-rays. In this embodiment, the lower limb radiographic filter 11a is provided with a rectangular filter 11c with lower transmission factor of X-ray near the center, so that the X-ray flux transmitted through the lower limb radiographic filter 11a is restricted to the square shape with the rectangular hole near center thereof. In this embodiment, the filter 11c has the rectangular shape, but the filter 11c is not limited to the rectangular filter 11c. For example, the filter 11c may have an oval shape, which is disposed in the vicinity of the center in the lower limb radiographic filter 11a, corresponding to the portion between both legs.

When the motor 22 revolves the drive shaft 20 around the axial center, the drive gear 17 is revolved, and the base gear 16 fitted with the drive gear 17 is also revolved. Each filter 11a, 11b disposed in the base gear 16 is revolved in the direction of the arrow b in FIG. 4 around the axial center of the base shaft 19 by the revolution of the base gear 16. Further, the revolution counter 23 measures the number of revolutions of the position detecting gear 18 fitted with the base gear 16 via the detection shaft 21, whereby the position of each filter 11a, 11b revolved in the direction of the arrow b in FIG. 4 is detected.

Each filter 11a, 11b is moved outside or inside the opening portion 10b of the X-ray movable restriction 10, namely, outside or inside the radiation field of the X-rays by revolving the base gear 16, as shown in FIG. 4. A certain filter 11 is selected from among the four filters (lower limb radiographic filter 11a, additional filters 11b) by revolving the base gear 16 every 90° and switched. Accordingly, the switching mechanism 12 corresponds to a movement mechanism in this invention, as well as switching member in this invention.

Figure 6:
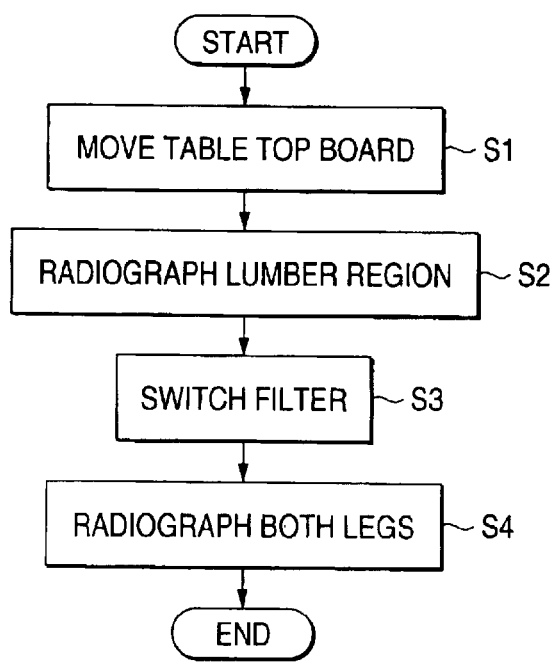
FIG. 6 is a flowchart showing a series of the X-ray radiography involved in the angiography of the lower limb.

Referring now to a flowchart of FIG. 6, an X-ray radiographic method involving the angiography for lower limb will be described below. In this embodiment, an X-ray radiography is performed in the order from the lumber region to the toe with the contrast medium flowing inside the blood vessel.

(Step S1) Movement of the Table Top Board

After the subject M is laid on the table top board 1, the table top board is moved up or down with the subject M laid thereon, so that the table top board 1 is positioned at a predetermined height. Then, the table top board 1 is moved along the direction of the body axis of the subject M, so that the lumber region of the subject M is located between the X-ray tube 5 and I.I 6 for the C-type arm 3.

(Step S2) Radiography of the Lumber Region

If the lumber region of the subject M is located between the X-ray tube 5 and I.I 6 for the C-type arm 3, it is started to radiograph the lumber region. Then, the additional filters 11b other then the lower limb radiographic filter 11a are located within the radiation field of X-rays, namely, the lower limb radiographic filter 11a is located outside the radiation field, whereby the lumber region is radiographed by transmitting the X-rays through the additional filters 11b inside the radiation field, as shown in FIG. 5A. More specifically, the X-rays are radiated from the X-ray tube 5, and via the additional filters 11b and the X-ray movable restriction 10 to the subject M. The X-rays applied to the subject M are detected and converted into an optical image by I.I 6. The converted data is transferred via the control section 14 to the arithmetical operation section 15 for performing various arithmetical operations to acquire a radiographed image of the lumber region. In this embodiment, since it is intended to examine how the contrast medium flows inside the blood vessel, an output result of the radiographed image is displayed on a TV monitor (not shown) and examined without actually acquiring the radiographed image.

The table top board 1 is moved in a direction of the head of the subject M, to acquire the radiographed image from the lumber region to the toe, while examining the radiographed image of the lumber region. The radiographed image is acquired in the order while the table top board 1 is being moved.

(Step S3) Switch of the Filter

If the groin (crotch of the thigh) of the subject M reaches the position between the X-ray tube 5 and I.I 6, the switching mechanism 12 switches the filter 11. That is, the relative position between the holding member and the table top board in this invention means the relative position between the C-type arm 3 and the table top board 1 where a region of the subject M on the toe side from the groin is located between the X-ray tube 5 and I.I 6 for the C-type arm 3.

In switching, the additional filters 11b inside the radiation field are revolved in a direction of the arrow in FIG. 5B, and moved outside the radiation field as shown in FIG. 5B. Instead, the lower limb radiographic filter 11a, which is located outside the radiation filed, is revolved in the same direction and moved inside the radiation field as shown in FIG. 5B. Thereby, the lower limb radiographic filter 1a is selected and switched. The revolution counter 23 detects the position of the filter 11, whereby the lower limb radiographic filter 11a is controlled to be located inside the radiation field.

(Step S4) Radiography of Both Legs

After the lower limb radiographic filter 11a is switched, it is started to radiograph both legs. In radiographing both legs, the X-rays are passed through the lower limb radiographic filter 11a inside the radiation field. More specifically, of an X-ray flux radiated from the X-ray tube 5, the X-rays near the center are hardly transmitted by the rectangular filter 11c near the center of the lower limb radiographic filter 11a, and the X-rays in other portions are transmitted. Thereby, the X-ray flux transmitted through the lower limb radiographic filter 11a is applied to the subject M in a restricted state of square shape with the rectangular hole near the center thereof. Accordingly, the X-rays are applied to a portion of the leg of the subject M corresponding to the position of square shape of the lower limb radiographic filter 11a, but hardly applied to a portion between both legs corresponding to the vicinity of the center of the lower limb radiographic filter 11a, or the rectangular filter 11c.

The radiographed image of both legs is displayed on the TV monitor and examined, on the basis of the data of the X-rays applied to both legs of the subject M in the same manner as radiography of the lumber region in step S2.

The table top board 1 is moved in a direction of the head of the subject M, to acquire the radiographed image from the groin to the toe, while examining the radiographed image of both legs. The radiographed image is acquired in the order while the table top board 1 is being moved.

If the radiographed image is acquired up to the toe, the table top board 1 with the subject M laid thereon is moved along the body axis of the subject M to avoid the C-type arm 3. After the table top board 1 is moved up or down, the subject M is let off the table top board 1, whereby the series of X-ray radiography is ended.

In the series of X-ray radiography according to the steps S1 to S4, to acquire the radiographed image of both legs using the lower limb radiographic filter 11a in step S4, the lower limb radiographic filter 11a is moved inside the radiation field in step S3, only when both legs are radiographed, thereby performing an X-ray radiography of both legs of the subject M through the filter 11a. To acquire the radiographed image of the lumber region in step S2, other than both legs, without employing the filter 11a, the filter 11a is moved outside the radiation field, thereby performing an X-ray radiography of the lumber region of the subject M without the filter 11a.

In the apparatus of this embodiment, the switching mechanism 12 is configured to move the filter 11 outside or inside the radiation field of X-rays radiated from the X-ray tube 5. Also, when the relative position between the C-type arm 3 and the table top board 1 is at the predetermined position, where a region of the subject M on the toe side from the groin is located between the X-ray tube 5 and I.I 6 for the C-type arm 3 in this embodiment, the lower limb radiographic filter 11a of the four filters is moved inside the radiation field, while the relative position is not at the predetermined position, the filter 11a is moved outside the radiation field.

In this embodiment, when radiographing both legs, the X-rays are applied to a portion of the leg of the subject M corresponding to the position of square shape of the lower limb radiographic filter 11a, but hardly applied to a portion between both legs corresponding to the vicinity of the center of the lower limb radiographic filter 11a, or the rectangular filter 11c, reducing a difference in the transmission factor between the leg portion and the portion between both legs. Consequently, no halation occurs, whereby there is no need for placing a mat over the subject M to prevent the halation, and it is possible to lighten a burden on the operator.

Further, when radiographing the lumber region of the subject M, for example, other than both legs, the additional filters 11b are employed in place of the lower limb radiographic filter 11a, so that the center of the radiographed image of the lumber region is not hidden by the rectangular filter 11c in the lower limb radiographic filter 11a. Consequently, it is possible to select whether or not to employ the lower limb radiographic filter 11a depending on the radiographing position, facilitating the radiography, whereby the X-ray radiographic apparatus with high universality is realized.

In this embodiment, the switching mechanism 12 has means for selecting and switching the lower limb radiographic filter 11a from among the four filters 11, whereby the X-ray radiography is made using various filters.

This invention is not limited to the above embodiment, but may be modified or varied in the following manner.

(1) In the above embodiment, a contrast medium is injected via a contrast medium injecting catheter, and it is examined how the contrast medium flows inside the blood vessel. However, this invention is also applicable to a digital subtraction angiography in which the radiographed images before and after catheter injection are subject to a subtraction operation. Also, this invention is applicable to an X-ray radiographic apparatus for simply performing the X-ray radiography for medical examination without catheter injection, and an X-ray CT apparatus.

(2) In the above embodiment, the filters 11 to be switched are the lower limb radiographic filter 11a and the additional filters 11b, but not limited to those filters 11a and 11b. Also, the lower limb radiographic filter 11a is only provided in the base gear 16, but when the filter 11a is not employed, the X-ray radiography may be made without any use of other filters.

Figure 7:
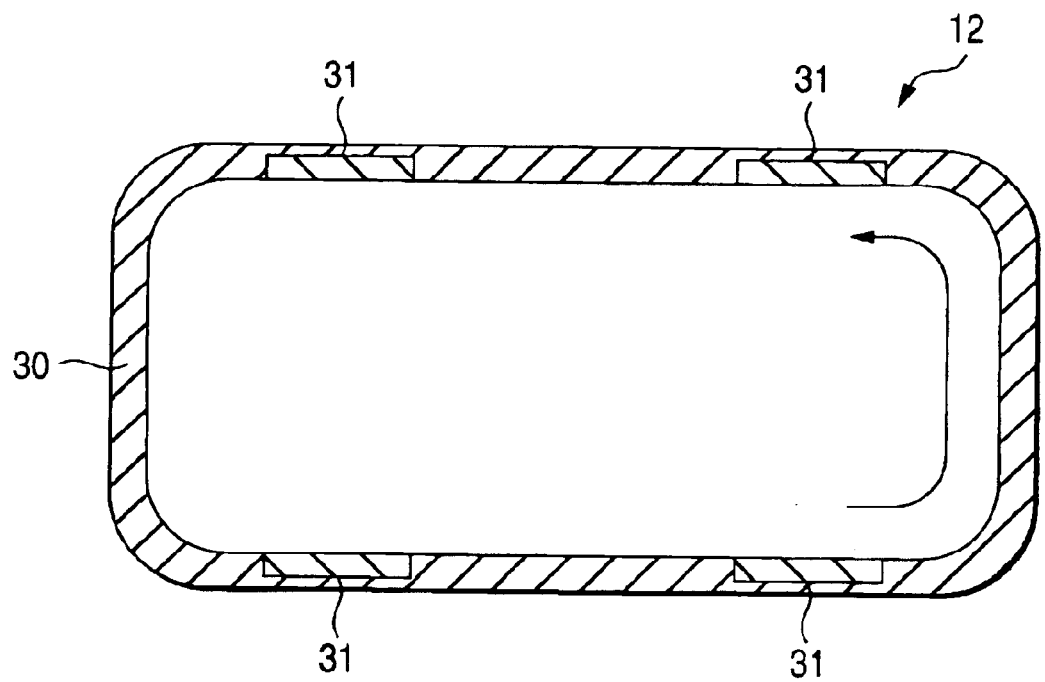
FIG. 7 is a cross-sectional view of one variation of the switching mechanism.

(3) In the above embodiment, the switching mechanism 12 is employed as movement mechanism of this invention, and has the function of the switching member in this invention, but the switching member is not limited to the switching mechanism 12 in this embodiment. For example, a plurality of filters 31 are disposed on the belt 30, as shown in a cross-sectional view of FIG. 7, and the filters 31 are selected and switched by moving the belt 30 in a direction of the arrow in FIG. 7.

Figure 8:
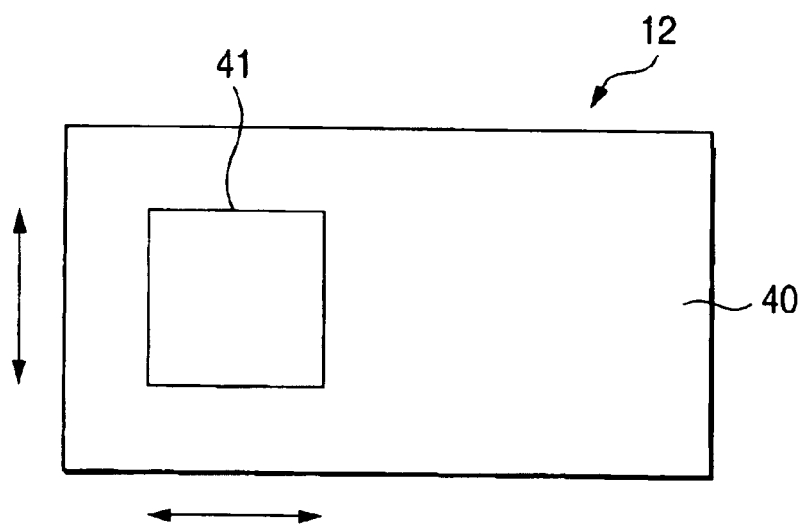
FIG. 8 is a plan view of another variation of the switching mechanism.

Also, it does not necessarily follow that the function of switching member is provided. The lower limb radiographic filter 11a may be moved outside or inside the radiation field by providing the lower limb radiographic filter 11a alone in the base gear 16 as described in the variation example (2). Alternatively, a single filter 41 may be disposed on a base board 40 movable in the horizontal direction, in place of the base gear 16 of this embodiment, whereby the filter 41 may be moved outside or inside the radiation field by moving the base board 40 in the horizontal direction, as shown in a plan view of FIG. 8.

(4) In the above embodiment, the switching mechanism 12 as the movement mechanism in this invention is provided in the collimator 9 that is the X-ray restrictor in this invention, but the movement mechanism in this invention may be provided in the X-ray tube 5.

(5) In the above embodiment, the holding member in this invention uses the C-type holding member 3 with the C-type arm 8, but is not specifically limited as long as the holding member holds the X-ray tube and the X-ray detector.

As will be apparent from the above description, with the invention of the first aspect, the movement mechanism is configured such that the filter is moved inside the radiation field, only when the relative position between the holding member and the table top board is at a predetermined position, or the filter is moved outside the radiation field, when the relative position is other than the predetermined position. Consequently, it is possible to lighten a burden of the operator, whereby the X-ray radiographic apparatus has a higher universality.

What is claimed is:

1. An X-ray radiographic apparatus comprising:
    an X-ray tube for radiating X-rays to a subject;
    an X-ray detector for detecting an X-ray applied to the subject;
    a holding member for holding said X-ray tube and said X-ray detector;
    a table top board for laying the subject thereon;
    a filter for extracting X-ray components radiated from said X-ray tube; and
    a movement mechanism for moving said filter outside or inside a radiation field of the X-rays radiated from said X-ray tube so that said filter is moved inside said radiation field only when the relative position between said holding member and said table top board is at a predetermined position, and said filter is moved outside said radiation field when said relative position is other than said predetermined position.

2. The X-ray radiographic apparatus according to claim 1, wherein said filter restricts an X-ray flux radiated from said X-ray tube in a predetermined shape.

3. The X-ray radiographic apparatus according to claim 1, wherein said filter is a currently used filter and is one of a plurality of available filters and wherein said movement mechanism includes a switching member for switching said currently used filter with another of said plurality of available filters.

4. The X-ray radiographic apparatus according to claim 2, wherein said filter is a currently used filter and is one of a plurality of available filters and wherein said movement mechanism includes a switching member for switching said currently used filter with another of said plurality of filters.

* * * * *